United States Patent [19]

Beckmann et al.

[11] Patent Number: 5,466,812
[45] Date of Patent: Nov. 14, 1995

[54] PREPARATION OF N-AMINOPYRIDONES

[75] Inventors: Stefan Beckmann, Mannheim; Ernst Schefczik, Ludwigshafen, both of Germany

[73] Assignee: BASF Aktiengesellschaft, Ludwigshafen, Germany

[21] Appl. No.: 255,752

[22] Filed: Jun. 7, 1994

[30] Foreign Application Priority Data

Jun. 14, 1993 [DE] Germany .................. 43 19 675.6

[51] Int. Cl.⁶ .................. C07D 213/57; C07D 213/84; C07D 213/85
[52] U.S. Cl. .................. 546/288; 546/261; 546/281; 546/283; 546/284; 546/294; 546/296
[58] Field of Search .................................. 546/288

[56] References Cited

FOREIGN PATENT DOCUMENTS 2150772  4/1973  Germany .
WO92/19684  11/1992  WIPO .

OTHER PUBLICATIONS

Polish Journal of Chemistry 58, Studies in the Field of Nitrogen Heterocyclic Compounds. Part XVI. A Novel "Dimroth Type" Rearrangement of some 1–amino–2–pyridone Derivatives, Roman Balicki, pp. 85–95, (1984).
Chemical Abstracts, vol. 83, No. 17, Oct. 27, 1975, AN 147421k, p. 494.
Chemical Abstracts, vol. 92, No. 25, Jun. 23, 1980, AN 215333w, p. 616.
Chemical Abstracts, vol. 114, No. 8, Feb. 25, 1991, AN 64264u, p. 113.

*Primary Examiner*—Alan L. Rotman
*Attorney, Agent, or Firm*—Oblon, Spivak, McClelland, Maier, & Neustadt

[57] ABSTRACT

A process for preparing pyridones of the formula I

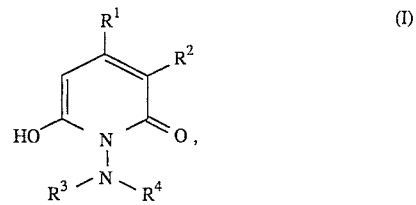

where $R^1$ is hydrogen, $C_1$–$C_6$-alkyl, $C_3$–$C_7$-cycloalkyl, $C_3$–$C_4$-alkenyl or substituted or unsubstituted phenyl, $R^2$ is cyano, carbamoyl, carboxyl, $C_1$–$C_6$-alkoxycarbonyl, substituted or unsubstituted $C_1$–$C_6$-alkanoyl, substituted or unsubstituted benzoyl, halogen or nitro, $R^3$ is hydrogen, and $R^4$ is substituted or unsubstituted $C_1$–$C_{12}$-alkanoyl, $C_1$–$C_{12}$-alkoxycarbonyl, substituted carbamoyl, substituted or unsubstituted $C_1$–$C_{12}$-alkylsulfonyl, $C_5$–$C_7$-cycloalkylsulfonyl, substituted or unsubstituted arylsulfonyl or hetarylsulfonyl, substituted or unsubstituted arylcarbonyl or hetarylcarbonyl, or $R^3$ and $R^4$ together with the nitrogen atom joining them together are a heterocyclic radical, comprises reacting the carbonyl compounds of the formulae II and III

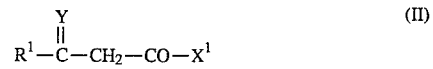

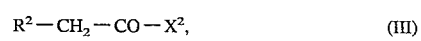

where Y is oxygen or imino and one of the radicals $X^1$ and $X^2$ is a radical of the formula $NH-NR^3R^4$ and the other is $C_1$–$C_6$-alkoxy, and $R^1$, $R^2$, $R^3$ and $R^4$ are each as defined above, in a diluent in the presence or absence of a base.

2 Claims, No Drawings

PREPARATION OF N-AMINOPYRIDONES

The present invention relates to a novel process for preparing N-amino-substituted 6-hydroxypyrid-2-ones by reacting acylated acetic hydrazines or esters with derivatives of acetic esters or hydrazides.

Polish J. Chem. 58 (1984), 85–95, discloses the preparation of N-amino-substituted 6-hydroxypyrid-2-ones which do not have any substituents on the amino group by reacting acylated acetic esters with cyanoacetic hydrazide.

It is an object of the present invention to provide a novel process for preparing N-amino-substituted 6-hydroxypyrid-2-ones in which the amino group is substituted by an acyl group introduced before the pyridone is formed, ie. not subsequently introduced into the ready-formed pyridone ring.

We have found that this object is achieved by a process for preparing pyridones of the formula I

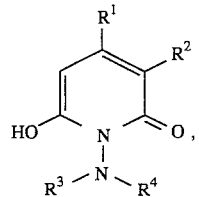
(I)

where
$R^1$ is hydrogen, $C_1$–$C_6$-alkyl, $C_3$–$C_7$-cycloalkyl, $C_3$–$C_4$-alkenyl or substituted or unsubstituted phenyl, $R^2$ is cyano, carbamoyl, carboxyl, $C_1$–$C_6$-alkoxycarbonyl, substituted or unsubstituted $C_1$–$C_6$-alkanoyl, substituted or unsubstituted benzoyl, halogen or nitro, $R^3$ is hydrogen, and $R^4$ is substituted or unsubstituted $C_1$–$C_{12}$-alkanoyl, $C_1$–$C_{12}$-alkoxycarbonyl, $C_1$–$C_{12}$-monoalkylcarbamoyl, substituted or unsubstituted monophenylcarbamoyl, substituted or unsubstituted $C_1$–$C_{12}$-alkylsulfonyl, $C_5$–$C_7$-cycloalkylsulfonyl, substituted or unsubstituted phenylsulfonyl, substituted or unsubstituted pyridylsulfonyl, substituted or unsubstituted benzoyl, pyridylcarbonyl or thienylcarbonyl, or $R^3$ and $R^4$ together with the nitrogen atom joining them together are unsubstituted or $C_1$–$C_4$-alkyl-substituted succinimido or unsubstituted or $C_1$–$C_4$-alkyl-substituted phthalimido,
which comprises reacting the carbonyl compounds of the formulae II and III

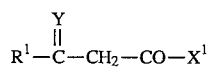
(II)

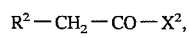
(III)

where Y is oxygen or imino and one of the radicals $X^1$ and $X^2$ is a radical of the formula NH—$NR^3R^4$ and the other is $C_1$–$C_6$-alkoxy, and $R^1$, $R^2$, $R^3$ and $R^4$ are each as defined above, in a diluent in the presence or absence of a base.

The abovementioned formulae do of course also comprehend the corresponding tautomeric forms of the individual compounds. Examples are:

Formula I

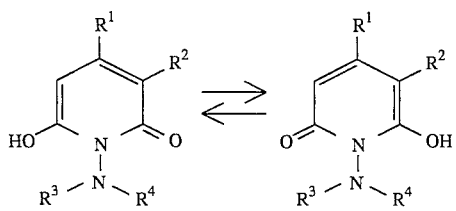

Formula II

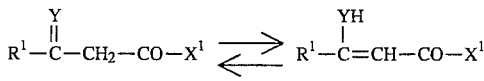

Formula III
(when $R^2$ is for example benzoyl)

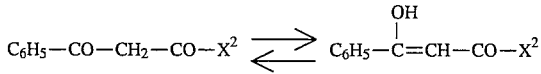

All the alkyl groups appearing in the abovementioned formulae can be not only straight-chain but also branched.

When substituted alkyl groups appear in the abovementioned formulae they can have as substituents for example cyano, phenyl, tolyl, $C_1$–$C_4$-alkoxy, $C_1$–$C_4$-alkanoyloxy, $C_1$–$C_4$-alkoxycarbonyl or $C_1$–$C_4$-alkoxycarbonyloxy wherein, in the latter case, the alkoxy group may be substituted by phenyl or $C_1$–$C_4$-alkoxy.

When substituted phenyl or pyridyl groups appear in the abovementioned formulae they may have as substituents for example $C_1$–$C_4$-alkyl or $C_1$–$C_4$-alkoxy.

$R^1$ is for example methyl, ethyl, propyl, isopropyl, butyl, isobutyl, sec-butyl, pentyl, isopentyl, neopentyl, tert-pentyl, hexyl, 2-methylpentyl, allyl, methallyl, cyclopropyl, cyclobutyl, cyclopentyl, cyclohexyl, methylcyclohexyl, cycloheptyl, phenyl, 2-methylphenyl, 2,4-dimethylphenyl, 2-methoxyphenyl or 2,4-dimethoxyphenyl.

$R^2$ and $R^4$ are each for example formyl, acetyl, propionyl, butyryl, isobutyryl, pentanoyl, hexanoyl, heptanoyl, octanoyl, 2-ethylhexanoyl, 2-methoxyacetyl, benzoyl, 2-, 3- or 4-methylbenzoyl, 2-, 3- or 4-methoxybenzoyl, methoxycarbonyl, ethoxycarbonyl, propoxycarbonyl, isopropoxycarbonyl or butoxycarbonyl.

$R^2$ may also be for example fluorine, chlorine or bromine.

$R^4$ may also be for example methylsulfonyl, ethylsulfonyl, propylsulfonyl, isopropylsulfonyl, butylsulfonyl, cyclopentylsulfonyl, cyclohexylsulfonyl, cycloheptylsulfonyl, phenylsulfonyl, tolylsulfonyl, pyridylsulfonyl, thien-2-ylcarbonyl, thien-3-ylcarbonyl, methylcarbamoyl, ethylcarbamoyl, propylcarbamoyl, isopropylcarbamoyl, butylcarbamoyl, phenylcarbamoyl or tolylcarbamoyl.

Preference is given to a process for preparing pyridones of the formula I where $R^1$ is hydrogen or $C_1$–$C_4$-alkyl, in particular methyl.

Preference is further given to a process for preparing pyridones of the formula I where $R^2$ is cyano, $C_1$–$C_4$-alkoxycarbonyl or $C_2$–$C_4$-alkanoyl, which may be phenyl- or $C_1$–$C_4$-alkoxy-substituted, in particular cyano.

Preference is further given to a process for preparing pyridones of the formula I where $R^3$ is hydrogen, and $R^4$ is $C_1$–$C_8$-alkanoyl, which may be $C_1$–$C_4$-alkoxy- or phenyl-substituted, $C_1$–$C_8$-monoalkylcarbamoyl, monophenylcarbamoyl, $C_1$–$C_8$-alkylsulfonyl, phenylsulfonyl, tolylsulfonyl, pyridylsulfonyl, benzoyl, methylbenzoyl, pyridylcarbonyl or thienylcarbonyl, or $R^3$ and $R^4$ together with the nitrogen atom joining them together are succinimido or phthalimido.

Particular preference is given to a process for preparing pyridones of the formula I where $R^3$ is hydrogen, and $R^4$ is $C_1$–$C_8$-alkanoyl which may be $C_1$–$C_4$-alkoxy- or phenyl-substituted, $C_1$–$C_8$-monoalkylcarbamoyl, monophenylcarbamoyl, benzoyl, methylbenzoyl or thienylcarbonyl.

Suitable diluents for use in the process of the invention include for example water or alcohols such as methanol, ethanol, propanol, isopropanol, butanol or isobutanol.

Suitable bases for use in the process of the invention include for example alkali metal hydroxides, such as lithium, sodium or potassium hydroxide, alkali metal carbonates, such as lithium, sodium or potassium carbonate, or alkali metal alkoxides, such as lithium, sodium or potassium methoxide, ethoxide or propoxide.

In the process of the invention the carbonyl compounds of the formulae II and III are generally used in a molar ratio of from 1:1 to 1:3, preferably from 1:1 to 1:2, in particular from 1:1 to 1:1.2.

Based on the weight of the carbonyl compounds II and III, generally from 100 to 1000% by weight, preferably from 200 to 500% by weight, of diluent and optionally from 10 to 500% by weight, preferably from 50 to 250% by weight, of base are used.

The process of the invention, which is generally carried out under atmospheric pressure, is generally carried out at from 0° to 150° C., preferably from 20° to 100° C.

The process of the invention is preferably carried out with water or $C_1$–$C_4$-alkanols, in particular methanol, ethanol, isopropanol or isobutanol, as solvent.

When the process of the invention is carried out in the presence of a base, the base is preferably sodium hydroxide, sodium methoxide or sodium ethoxide.

The novel process is advantageously carried out by charging the carbonyl compounds of the formulae II and III initially together with diluent, then if desired adding the base and thereafter stirring at the abovementioned temperature. (It is also possible first to charge a carbonyl compound together with the diluent and optionally the base and to add thereto the other carbonyl compound, generally the hydrazide.)

After 2–20 hours the reaction is generally complete and it is possible for the target product, if desired after dilution with water and acidification of the reaction mixture, to be separated off as a precipitate, which is washed and dried.

In a particular embodiment of the novel process, 1-benzoylamino-3-cyano-4-methyl-6-hydroxypyrid-2-one is prepared starting from a $C_1$–$C_4$-alkyl cyanoacetate and hydrazine in a one-pot process using water as reaction medium.

This is because we have further found an advantageous process for preparing the pyridone of the formula IV

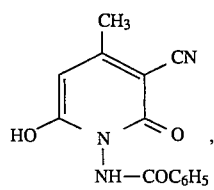

(IV)

which comprises a) in a first step, reacting a $C_1$–$C_4$-alkyl cyanoacetate with hydrazine in water as reaction medium to form a cyanoacetic hydrazide, then b) in a second step treating the as-synthesized cyanoacetic hydrazide with benzoyl chloride in the presence of a buffer system to form an N-benzoylcyanoacetic hydrazide, and thereafter c) in a third step reacting the as-synthesized N-benzoylcyanoacetic hydrazide with a $C_1$–$C_4$-alkyl acetoacetate in the presence of both a base and a phase transfer catalyst.

Suitable $C_1$–$C_4$-alkyl cyanoacetates and $C_1$–$C_4$-alkyl acetoacetates include for example the methyl, ethyl, propyl, isopropyl, butyl or isobutyl esters. The use of the respective methyl or ethyl ester is preferred.

The first step is generally carried out at from 0° to 50° C., preferably from 20° to 30° C.

The $C_1$–$C_4$-alkyl cyanoacetate and hydrazine are generally used in it in a molar ratio of from 1:1 to 1:3, preferably from 1:1 to 1:2, in particular from 1:1 to 1:1.1.

Based on the weight of the $C_1$–$C_4$-alkyl cyanoacetate, it is customary to use from 100 to 300% by weight, preferably from 200 to 250% by weight, of water as reaction medium.

After the cyanoacetic hydrazide has been formed, which generally takes about 8 hours, it is not intermediately isolated before it is treated with benzoyl chloride. This treatment generally takes place at from 0° to 50° C., preferably from 20° to 30° C., and in the presence of a buffer system, for example a phosphate buffer based on dipotassium hydrogenphosphate.

Per mole of $C_1$–$C_4$-alkyl cyanoacetate (in step 1) it is customary to use from 1 to 1.5 mol, preferably from 1 to 1.1 mol, of benzoyl chloride.

After the N-benzoylcyanoacetic hydrazide has been formed, which generally takes from 5 to 10 hours, it is not intermediately isolated before it is reacted with the $C_1$–$C_4$-alkyl acetoacetate. This reaction generally takes place at from 0° to 50° C., preferably from 20° to 30° C., in the presence of a phase transfer catalyst, for example trimethylbenzylammonium chloride or tetrabutylammonium chloride.

The reaction is further carried out in the presence of a base, in which case it is advantageous to maintain a reaction mixture pH from 9.5 to 10. Suitable bases include for example those mentioned above. The use of 20–50% strength by weight sodium hydroxide solution or potassium hydroxide solution is preferred.

Per mole of $C_1$–$C_4$-alkyl cyanoacetate (in step 1) it is customary to use from 1 to 3 mol, preferably from 1 to 2 mol, of $C_1$–$C_4$-alkyl acetoacetate.

The phase transfer catalyst is used in catalytic amounts, ie. for example from 0.01 to 0.2 mol, based on 1 mol of $C_1$–$C_4$-alkyl cyanoacetate (in step 1).

Following a reaction time from 10 to 20 hours, the reaction is complete and the resulting pyridone of the formula IV, after the reaction mixture has been acidified, for example with concentrated hydrochloric acid, is separated off, washed and dried.

The novel process produces the N-aminopyridones in a simple manner and in high yield and purity. This was unforeseeable, since the reaction of the multifunctional reactants II and III would have been expected to lead to the increased formation of by-products (competing products).

The pyridones of the formula I are useful intermediates for producing pyridone dyes as described for example in WO-A-92/19684.

The Examples which follow illustrate the invention.

EXAMPLE 1

99 g of methyl cyanoacetate and 220 g of N-benzoyl acetoacetic hydrazide were introduced into 500 ml of methanol. 180 g of 30% strength by weight methanolic sodium methoxide solution were added dropwise with stirring and the mixture was then heated under reflux for 6 hours. After cooling, the precipitated product was filtered off with suction and washed with methanol to leave, after drying, 235 g of a compound of the formula

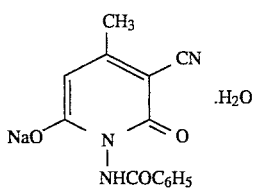

having a melting point from 328° to 329° C. (from methanol).

| Analysis for $C_{14}H_{12}N_3NaO_4$ (309) | | | | | |
|---|---|---|---|---|---|
| calculated: | C 54.3 | H 3.9 | N 13.6 | N 7.4 | O 20.7 |
| found: | 54.5 | 4.1 | 13.5 | 7.2 | 20.9 |

By means of strong mineral acids (eg. hydrochloric acid) it is possible to convert the salt into the free hydroxy compound of the formula

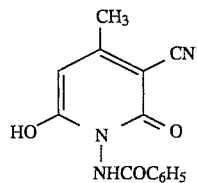

A sample recrystallized from γ-butyrolactone melts at from 252° to 253° C. and has the following analysis:

| $C_{14}H_{11}N_3O_3$ (269) | | | | |
|---|---|---|---|---|
| calculated: | C 62.4 | H 4.1 | N 15.6 | O 17.8 |
| found: | 62.2 | 4.2 | 15.3 | 18.1 |

EXAMPLE 2

Example 1 was repeated with the methyl cyanoacetate replaced by an equivalent amount of dimethyl malonate, affording 199 g of the compound of the formula

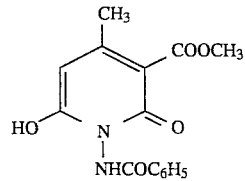

A sample recrystallized from acetic acid has a melting point from 212° to 213° C. and the following analytical values:

| $C_{15}H_{14}N_2O_5$ (302) | | | | |
|---|---|---|---|---|
| calculated: | C 59.6 | H 4.7 | N 9.3 | O 26.5 |

| -continued | | | | |
|---|---|---|---|---|
| $C_{15}H_{14}N_2O_5$ (302) | | | | |
| found: | 59.8 | 4.8 | 9.1 | 26.9 |

EXAMPLE 3

Example 1 was repeated with the methyl cyanoacetate replaced by an equivalent amount of methyl acetoacetate, affording 228 g of the compound of the formula

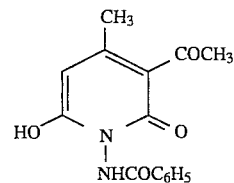

having a melting point from 239° to 249° C. (from acetic acid).

| Analytical values: $C_{15}H_{14}N_2O_4$ (286) | | | | |
|---|---|---|---|---|
| calculated: | C 62.9 | H 4.9 | N 9.8 | O 22.3 |
| found: | 62.9 | 5.0 | 9.6 | 22.2 |

EXAMPLE 4

Example 1 was repeated with the methyl cyanoacetate replaced by an equivalent amount of methyl methoxyacetate, affording 187 g of the compound of the formula

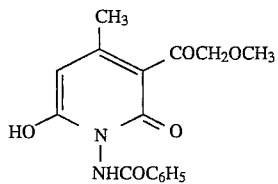

A sample recrystallized from pentanol melts at from 194° to 195° C. and has the following analytical values:

| $C_{16}H_{16}N_2O_5$ (316) | | | | |
|---|---|---|---|---|
| calculated: | C 60.7 | H 5.1 | N 8.9 | O 25.3 |
| found: | 60.5 | 5.2 | 8.8 | 25.7 |

EXAMPLE 5 a) 198 g of cyanoacetic hydrazide were dissolved in 1000 ml of water at 50° C. and admixed with 296 g of phthalic anhydride added a little at a time. After stirring at 50° C. for 4 hours, the mixture was cooled down with ice and filtered with suction, and the filter residue was dried to leave 386 g of N-cyanoacetyl-N'-phthaloylhydrazine in the form of colorless crystals having a melting point from 291° to 292° C. (from ethanol).

b) To 1500 ml of ethanol were added 229 g of the N-cyanoacetyl-N'-phthaloylhydrazine obtained under a) and 115 g of methyl 3-aminocrotonate, and the mixture was refluxed for 8 hours. It was then adjusted to pH 1 with dilute hydrochloric acid, and ethanol was distilled off with steam. After cooling, the suspension was filtered with suction and the product obtained was washed with water and dried to leave 232 g of the compound of the formula

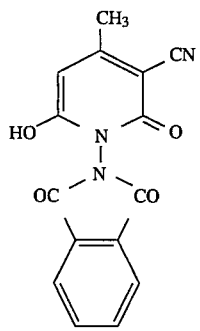

in the form of colorless crystals having a melting point from 267° to 268° C. (from butyrolactone).

| Analysis for $C_{15}H_9N_3O_4$ (295) | | | | |
|---|---|---|---|---|
| calculated: | C 61.0 | H 3.1 | N 14.2 | O 21.7 |
| found: | 60.8 | 3.2 | 14.1 | 22.2 |

EXAMPLE 6

To 1000 ml of isopropanol were added 115 g of methyl 3-aminocrotonate and 218 g of N-cyanoacetyl-N'-phenylaminocarbonylhydrazine, and the mixture was refluxed for 8 hours. After cooling, the precipitated product was filtered off with suction, washed with acetone and dried to leave 218 g of the compound of the formula

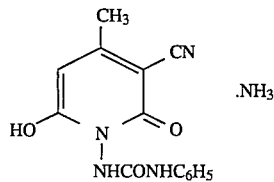

A sample recrystallized from N,N-dimethylformamide melts at from 248° to 249° C. and has the following analysis:

| $C_{14}H_{15}N_5O_3$ (301) | | | | |
|---|---|---|---|---|
| calculated: | C 55.8 | H 5.0 | N 23.3 | O 15.9 |
| found: | 55.5 | 5.1 | 23.2 | 16.2 |

EXAMPLE 7

To 750 ml of isobutanol were added 115 g of methyl 3-aminocrotonate and 198 g of N-cyanoacetyl-N'-butylaminocarbonylhydrazine, and the mixture was refluxed for 6 hours. It was then acidified with dilute hydrochloric acid, and the isobutanol was distilled off with steam. After cooling, the product was filtered off with suction and washed with water to leave, after drying, 193 g of the compound of the formula

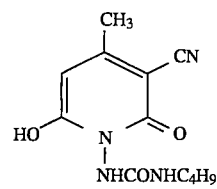

A sample recrystallized from acetic acid melts at from 204° to 205° C. and has the following analysis:

| $C_{12}H_{16}N_4O_3$ (264) | | | | |
|---|---|---|---|---|
| calculated: | C 54.5 | H 6.1 | N 21.2 | O 18.2 |
| found: | 54.3 | 6.2 | 21.2 | 18.2 |

EXAMPLE 8

To 800 ml of isopropanol were added 120 g of methyl 3-aminocrotonate and 225 g of the compound of the formula

and the mixture was refluxed for 8 hours. After cooling, it was diluted with twice the volume of water and acidified with hydrochloric acid to a pH from 1 to 2. After standing overnight the precipitated product was filtered off with suction, washed with water and dried under reduced pressure to leave 237 g of the compound of the formula

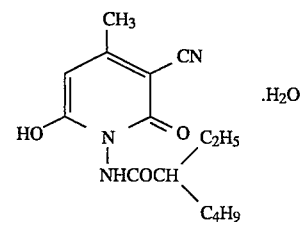

The compound does not give up the water of crystallization even on recrystallization from ethanol; melting point from 199° to 200° C.

| Analysis: $C_{15}H_{23}N_3O_4$ (309) | | | | |
|---|---|---|---|---|
| calculated: | C 58.3 | H 7.4 | N 13.6 | O 20.7 |
| found: | 58.3 | 7.5 | 13.6 | 20.8 |

EXAMPLE 9

To 900 ml of absolute ethanol were added 130 g of ethyl acetoacetate and 54 g of solid sodium methoxide. This was followed by 217 g of N-cyanoacetyl-N'-phenylacetylhydrazine, and the mixture was refluxed for 8 hours. After cooling, the reaction mixture was discharged onto ice-water and excess hydrochloric acid, and the mixture was stirred overnight. Filtering off with suction and drying left 228 g of the compound of the formula

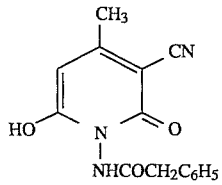

A sample recrystallized from acetic acid melts at from 232° to 233° C. and has the following analysis:

| $C_{15}H_{13}N_3O_3$ (283) | | | | |
|---|---|---|---|---|
| calculated: | C 63.6 | H 4.6 | N 14.8 | O 16.9 |
| found: | 63.3 | 4.8 | 14.6 | 17.3 |

EXAMPLE 10

5 g of hydrazine hydrate were added dropwise with ice-cooling to a mixture of 10 ml of water and 9.9 ml of methyl cyanoacetate. The mixture was subsequently stirred at room temperature for 5 hours. Then 8.7 g of dipotassium hydrogenphosphate, dissolved in 40 ml of water, were added to it. The reaction mixture was then cooled down to from −5° to 0° C. and admixed dropwise with 14.05 g of benzoyl chloride. The mixture was then warmed to room temperature and admixed with 13.5 ml of 25% strength by weight sodium hydroxide solution, producing a pH of 9.9. 1.9 g of trimethylbenzylammonium chloride and 10.8 ml of methyl acetoacetate were added, which produced a pH of 9.3. The reaction mixture was stirred at room temperature for 20 min and thereafter admixed with 24 ml of 25% strength by weight sodium hydroxide solution, producing a pH of 10, and subsequently stirred at room temperature for a further 5 hours. Then a further 7.6 ml of methyl acetoacetate and a further 2 ml of 25% strength by weight sodium hydroxide solution were added. After subsequently stirring for 3.5 hours the reaction mixture was admixed with 25 ml of concentrated hydrochloric acid and the resulting precipitate was filtered off with suction, washed with water and dried to leave 20.2 g of the pyridone of the formula

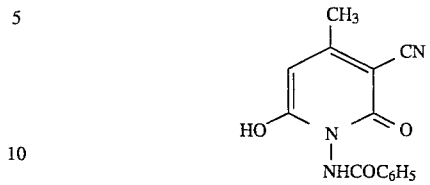

(melting point: 247° C.).

We claim:

1. A process for preparing the pyridone of the formula IV

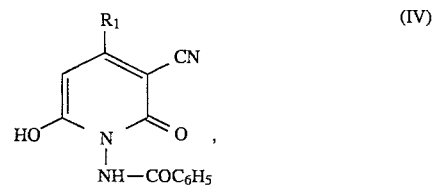

wherein $R_1$ is a $C_1$–$C_4$-alkyl, comprising the steps of:

(a) reacting a $C_1$–$C_4$-alkyl cyanoacetate with hydrazine in water as reaction medium to form a cyanoacetic hydrazide;

(b) treating said cyanoacetic hydrazide of step (a) with benzoyl chloride in the presence of a buffer system to form an N-benzoylcyanoacetic hydrazide, and thereafter;

(c) reacting said N-benzoylcyanoacetic hydrazide of step (b) with a $C_1$–$C_4$-alkyl acetate in the presence of both a base and a phase transfer catalyst to produce said pyridone of formula IV;

wherein step (c) is maintained at a basic pH; and wherein said phase transfer catalyst is a quaternary ammonium phase transfer catalyst.

2. The process of claim 1, wherein $R_1$ is a methyl radical; said pH is between 9.5 and 10; and said phase transfer catalyst is trimethylbenzylammonium chloride.

* * * * *